United States Patent
Zoromski et al.

(10) Patent No.: US 8,008,395 B2
(45) Date of Patent: *Aug. 30, 2011

(54) ORGANIC-INORGANIC HYBRID PARTICLE MATERIAL AND POLYMER COMPOSITIONS CONTAINING SAME

(75) Inventors: Michele Zoromski, Minneapolis, MN (US); Liliana Atanasoska, Edina, MN (US); Scott Schewe, Eden Prairie, MN (US); Mark Wolters, St. Paul, MN (US); Robert Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1624 days.

This patent is subject to a terminal disclaimer.

(21) Appl. No.: 11/235,743

(22) Filed: Sep. 27, 2005

(65) Prior Publication Data

US 2007/0072978 A1 Mar. 29, 2007

(51) Int. Cl.
*C08K 3/34* (2006.01)
*C08L 67/00* (2006.01)
*C08G 69/26* (2006.01)

(52) U.S. Cl. ........ 524/601; 524/493; 524/606; 525/420; 624/915

(58) Field of Classification Search ............ 523/200, 523/105; 524/492, 493, 495, 500, 504, 601, 524/606; 604/915; 623/1.15; 501/134; 424/423; 525/420, 446
See application file for complete search history.

(56) References Cited

U.S. PATENT DOCUMENTS

| | | | |
|---|---|---|---|
| 2,490,691 A | 12/1949 | Langkammerer et al. | |
| 3,646,155 A | 2/1972 | Scott et al. | |
| 3,950,285 A | 4/1976 | Wolgemuth | |
| 4,574,133 A | 3/1986 | Umpleby | |
| 4,753,992 A | 6/1988 | Umpleby | |
| 4,950,779 A | 8/1990 | Wengrovius et al. | |
| 5,109,080 A | 4/1992 | Wang et al. | |
| 5,112,913 A * | 5/1992 | Horiuchi et al. | 525/133 |
| 5,178,158 A | 1/1993 | de Toledo | |
| 5,210,168 A | 5/1993 | Bergstrom et al. | |
| 5,252,654 A | 10/1993 | David et al. | 524/414 |
| 5,282,998 A | 2/1994 | Horn et al. | |
| 5,336,731 A | 8/1994 | Ondrus et al. | |
| 5,354,802 A * | 10/1994 | Shiwaku et al. | 524/494 |
| 5,556,383 A | 9/1996 | Wang et al. | |
| 5,714,257 A | 2/1998 | Shah et al. | |
| 5,830,182 A | 11/1998 | Wang et al. | |
| 5,840,387 A * | 11/1998 | Berlowitz-Tarrant et al. | 428/36.91 |
| 5,849,215 A | 12/1998 | Gin et al. | 252/299.01 |
| 5,948,314 A | 9/1999 | Geiss et al. | 252/62 |
| 5,948,946 A | 9/1999 | Harmer et al. | 585/669 |
| 5,951,941 A | 9/1999 | Wang et al. | |
| 5,977,204 A * | 11/1999 | Boyan et al. | 523/113 |
| 5,977,241 A | 11/1999 | Koloski et al. | 524/502 |
| 6,093,463 A * | 7/2000 | Thakrar | 428/36.9 |
| 6,140,445 A | 10/2000 | Su et al. | |
| 6,146,356 A * | 11/2000 | Wang et al. | 604/96 |
| 6,160,190 A | 12/2000 | Harmer et al. | 585/458 |
| 6,232,386 B1 | 5/2001 | Vargo et al. | 524/434 |
| 6,271,292 B1 | 8/2001 | Mager et al. | 524/261 |
| 6,323,277 B1 | 11/2001 | Petty et al. | |
| 6,395,226 B1 * | 5/2002 | Plunkett | 422/48 |
| 6,444,324 B1 | 9/2002 | Yang et al. | |
| 6,472,467 B1 | 10/2002 | Chiao | 524/755 |
| 6,545,097 B2 | 4/2003 | Pinchuk et al. | 525/240 |
| 6,548,590 B1 | 4/2003 | Koloski et al. | 524/492 |
| 6,569,958 B1 | 5/2003 | Gross et al. | |
| 6,586,502 B2 | 7/2003 | Wallace et al. | 523/220 |
| 6,599,664 B2 | 7/2003 | Ehrlich | 429/303 |
| 6,608,129 B1 | 8/2003 | Koloski et al. | 524/403 |
| 6,629,961 B1 | 10/2003 | Israelsson et al. | |
| 6,686,035 B2 | 2/2004 | Jiang et al. | 428/304.4 |
| 6,737,145 B1 | 5/2004 | Watanabe et al. | 428/64.4 |
| 6,794,052 B2 | 9/2004 | Schultz et al. | 428/500 |
| 6,825,260 B2 * | 11/2004 | Sievers et al. | 524/492 |
| 6,946,174 B1 | 9/2005 | Chen | |
| 7,365,126 B2 | 4/2008 | Atanasoska et al. | |
| 2004/0175406 A1 | 9/2004 | Schwarz | |
| 2004/0181206 A1 | 9/2004 | Chiu et al. | |
| 2005/0015105 A1 | 1/2005 | Tang et al. | |
| 2006/0020331 A1 | 1/2006 | Bates et al. | |
| 2006/0199876 A1 | 9/2006 | Troczynski et al. | |
| 2006/0230476 A1 | 10/2006 | Atanasoska et al. | |
| 2007/0072978 A1 * | 3/2007 | Zoromski et al. | 524/430 |
| 2009/0306769 A1 * | 12/2009 | Schewe et al. | 623/1.34 |

FOREIGN PATENT DOCUMENTS

EP 0661558 7/1995

(Continued)

OTHER PUBLICATIONS

Tecoflex. "Next-Bio Basics." pp. 1-2.*

(Continued)

*Primary Examiner* — Vasu Jagannathan
*Assistant Examiner* — Hannah Pak
(74) *Attorney, Agent, or Firm* — Vidas, Arrett & Steinkraus

(57) ABSTRACT

Particulate materials useful as fillers, reinforcing agents, radiopacifiers, or impact modifiers. The particulate material has an average particle size range of about 10,000 nm or less and comprises an organic-inorganic hybrid material that has a ceramic material network having organic polymer segments distributed throughout the ceramic network. The ceramic network may be prepared by a sol-gel technique. The particulate material may be compounded in thermoplastic polymer compositions useful in a variety of applications such as preparation of medical device components.

12 Claims, No Drawings

FOREIGN PATENT DOCUMENTS

| | | |
|---|---|---|
| JP | 09165441 | 6/1997 |
| WO | 94/23787 | 10/1994 |
| WO | 98/05269 | 2/1998 |
| WO | 98/46164 | 10/1998 |
| WO | 00/48552 | 8/2000 |
| WO | 00/55213 | 9/2000 |
| WO | 2004/005533 | 1/2004 |
| WO | 2005/014075 | 2/2005 |
| WO | 2005/082277 | 9/2005 |
| WO | 2005/087284 | 9/2005 |
| WO | 2006/107359 | 10/2006 |

OTHER PUBLICATIONS

Honma, et al., Solid State Ionics, vol. 118, p. 29-36, (1999).
Honma, et al., Solid State Ionics, vol. 120, p. 225-264, (1999).
Honma, et al., Journal of Membrane Science, vol. 185, p. 83-94, (2001).
Huang, Wilkes, Polymer, vol. 30, p. 2001-2012, (1989).
Young, et al., Polymer, vol. 43, p. 6101-6114, (2002).
de Zea Bermudez, et al., Chem. Mater., vol. 11, p. 569-580, (1999).
Yano, S., et al., Mater SciEngng, vol. C6, p. 75-90, (1998).
Correia, et al., Solid State Ionics, vol. 156, p. 85-93, (2003).
U.S. Appl. No. 09/689,139, filed Oct. 12, 2000, Chen.
U.S. Appl. No. 11/094,638, filed Mar. 30, 2005, Atanasoska et al.
U.S. Appl. No. 11/213,177, filed Aug. 26, 2005, Atanasoska et al.
U.S. Appl. No. 11/235,743, filed Sep. 27, 2005, Zoromski et al.
C. Lacroix et al., "Properties of PETG/EVA blends: 2. Study of reactive compatibilization by n.m.r. spectroscopy and linear viscoelastice properties," Polymer vol. 37 No. 14, (1996) 2949-2956.
Sang-Hoon Rhee, "Bone-like apatite-forming ability and mechanical properties of poly(ε-caprolactone)/silica hybrid as a function of poly(ε-caprolactone) content," Biomaterials 25 (2004) 1167-1175.
V. Bounor-Legare et al., "New transecterification between ester and alkoxysilane groups: application to ethylene-co-vinyl acetate copolymer crosslinking," Polymer 43 (2002) 6085-6092.
V. Bounor-Legare et al., "Ethylene-co-vinyl acetate copolymer crosslinking through ester-alkoxysilane exchange reaction catalyzed by dibutyltin oxide: mechanistic aspects investigated through model compounds by multinuclear NMR spectroscopy," Polym. Int. 53: 484-494 (2004).
Y. Goutille et al., "Crosslinking in the melt of EVA using tetrafunctional silane: gel time from capillary rheometry," Polymer 44 (2003) 3165-3171.

V. Bounor-Legare et al., "A new route for organic-inorganic hybrid material syntheses through reactive processing without solvent," Polymer 45 (2004) 1485-1493.
A. Lambert III, "[Poly(ethylene terephthalate) ionomer]/Silicate Hybrid Materials via Polymer-In Situ Sol-Gel Reactions," Journal of Applied Polymer Science, vol. 84, pp. 1749-1761 (2002).
G. Kickelbick, "Concepts for the incorporation of inorganic building blocks into organic polymers on a nanoscale," Prog. Polym. Sci., 28 (2003) 83-114.
J. Pyun et al., "Synthesis of Nanocomposite Organic/Inorganic Hybrid Materials Using Controlled/"Living" Radical Polymerization," Chem Mater, 13:3436-3448 (2001).
K. Haas et al., "Hybrid Inorganic/Organic Polymers with Nanoscale Building Blocks: Precursors, Processing, Properties and Applications," Rev. Adv. Mater. Sci. 5 (2003) 47-52.
L. Matejka et al., "Block-copolymer organic-inorganic networks. Structure, morphology and thermomechanical properties," Polymer 45 (2004) 3267-3276.
L. Shen et al., "In situ polymerization and characterization of polyamide-6/silica nanocomposites derived from water glass," Polymer International, 53:1153-1160 (2004).
P. Xu, "Polymer-Ceramic Nanocomposites," Encyclopedia of Materials: Science and Technology, Elsevier Science Ltd. (2000).
R. Zoppi et al., "Hybrids of Poly(ethylene oxide-b-amide-6) and ZrO2 Sol-gel: Preparation, Characterization, Application in Processes of Membranes Separation," Advances in Polymer Technology, vol. 21, No. 1, pp. 2-16 (2002).
M. L. Sforça et al., "Hybrid Membranes Based on SiO2/Polyether-b-Polyamide: Morphology and Applications," Journal of Applied Polymer Science, vol. 82, pp. 178-185, 2001.
V. Munchow et al., "Poly[(oligoethylene glycol) dihidroxytitanate] as organic-inorganic polymer-electrollytes," Electrochimica Acta, 45 (2000) 1211-1221.
Masuru Okabe et al., "Phenomenological Study on Sol-Gel Transition of Linear Low Density Polyethylene in Organic Solvents," 1985, Journal of Applied Science, vol. 30, pp. 4735-4743.
Park et al., "A Paclitaxel-eluting Stent for the Prevention of Coronary Restenosis," ACC Current Journal Review, 2003, p. 65.
PCT Written Opinion for PCT/US2006/000727; which claims priority to U.S. Appl. No. 11/094,638, (Sep. 30, 2007).

* cited by examiner

ORGANIC-INORGANIC HYBRID PARTICLE MATERIAL AND POLYMER COMPOSITIONS CONTAINING SAME

BACKGROUND OF THE INVENTION

Ceramic sol-gel compositions that have sites that will crosslink into a polymer network are known. Such compositions may be formulated with cureable monomers to produce radiation curing compositions, for instance.

Compositions of thermoplastic polymers and particulate ceramic and metal nano-particles particles are known. For instance, fumed and colloidal silicas have wide uses in polymer compositions as fillers and reinforcing agents. Nanocomposite thermoplastic materials are typically made by mechanically mixing nanoparticles with the thermoplastic resin in a compounding process. However dispersion is often difficult, particularly in viscous melt or rubbery compositions of thermoplastic high polymers. The particulate materials will often agglomerate or clump when processed or blended into the base material. Furthermore, often it is difficult to achieve desired physical properties without sacrificing other desired properties. Using such particles to increase tensile properties of the polymer composition often produces an undesirable loss of flexibility, for instance. Additionally, many of these compositions are susceptible to a loss of desired properties upon aging.

There exists a need therefore for improved particulate materials useful in thermoplastic high polymer compositions that provide a wider range of physical property improvement benefits than are currently available.

U.S. patent application Ser. No. 11/094,638, filed Mar. 30, 2005, incorporated herein by reference in its entirety, describes polymeric/ceramic composite materials for use in medical devices polymer and sol-gel derived ceramic. The polymer and sol-gel ceramic may form a bi-continuous nanophase or separate polymeric and sol-gel derived ceramic phases.

SUMMARY OF THE INVENTION

The present application pertains to novel particulate form materials useful as fillers, reinforcing agents, radioopacifiers, impact modifiers, or the like, in compositions of thermoplastic high polymers and to thermoplastic polymer compositions comprising such particulate materials.

The novel particulate materials may have improved dispersion characteristics relative to currently available materials and/or may prevent the agglomeration of the desired nanoparticle in thermal processing. These benefits may be obtained by functionalizing a ceramic particle material comprising an inorganic ceramic network with organic polymer segments that interpenetrate the ceramic network. Optionally the polymer segments may also be covalently linked into the ceramic network. The materials may be made by known organic-inorganic sol-gel processing techniques, following which the materials are processed into particles of suitable size for compounding.

When compounded with thermoplastic high polymer materials the presence of the interpenetrating polymer segments in the particulate material modifies the particle/thermoplastic interface, which suitably compatibilizes the particle and polymer materials and can reduces the tendency to agglomerate during thermal processing of the composition.

In one aspect the invention is directed to a particulate material having an average particle size range of about 1 nm to about 10,000 nm that comprises a ceramic/polymer material, the ceramic/polymer material comprising a ceramic material network, the ceramic material network having a organic polymer segments distributed throughout the ceramic network.

In another aspect the invention is directed to a composition comprising a thermoplastic polymer and a particulate material as described herein.

The polymer/particulate compositions may be utilized to prepare medical components to alter physical properties such as, burst, distension, tensile, flexibility, abrasion resistance, fatigue resistance and/or toughness properties of the component. Therefore, in further aspects, the invention is directed to components prepared from the compositions disclosed herein.

These and other aspects of the invention will be apparent to the skilled person from the disclosure herein.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The particulate material of the invention is an organic-inorganic hybrid material. The organic part may be a polymer provided to the composition in solution with a solvent compatible with the ceramic sol, generated in-situ during the sol-gel processing or generated by a separate polymerization reaction run after the ceramic has been produced by the sol-gel reaction. If some of the components used to formulate the ceramic are functionalized with polymerizable groups, or if the organic polymers are functionalized with groups co-condensable with the ceramic in the sol-gel processing, the interpenetrate polymer may also crosslink the inorganic ceramic network.

Ceramic materials typically are networks of metal or semi-metal oxides or mixed oxide compounds. Examples of suitable metals and semi-metals include silicon, iron, vanadium, barium, zirconium, titanium, aluminum, tin, hafnium, rubidium, bismuth, strontium, tantalum, molybdenum, tungsten, rhenium, ruthenium, and/or iridium oxides, among others. In general, metal/semi-metal atoms (designated generally herein as M) within the ceramic phases are linked to one another via covalent linkages, such as M-O-M linkages, although other interactions are also commonly present including, for example, hydrogen bonding due to the presence of hydroxyl groups such as residual M-OH groups within the ceramic phases. Most typically the ceramic material will be based primarily on silicon oxide. Appropriate selection of additional or alternative components of the ceramic material, however, may be used to provide the particles of the invention with radiopacity, magneto-opacity, selective gas or liquid permeability, specific density or other desirable properties. In some cases the ceramic network includes linkages to organic groups, typically via a carbon or oxygen atom linkage.

The ceramic employed in the present invention is beneficially formed using a sol-gel technique. In sol-gel techniques, the precursor materials used are typically inorganic metallic and semi-metallic salts, metallic and semi-metallic complexes/chelates (e.g., metal acetylacetonate complexes), metallic and semi-metallic hydroxides, or organometallic and organo-semi-metallic compounds (e.g., metal alkoxides and silicon alkoxides and acyloxides). Silicon alkoxides and acyloxides are beneficial due to the variety of formulation options, including co-condensation with related compounds having strong stable C—Si bonds and which can form a strong link between the polymeric and ceramic networks.

In some embodiments the organic-inorganic material is prepared by compounding a sol-gel ceramic precursor, optionally functionalized with an organic linking group, with a polymer component at elevated temperature, and subsequently processing the composition in a sol-gel technique to condense the ceramic network. If the ceramic precursor is functionalized with an organic linking group, such as isocyanate epoxy, a carbon-linked amino group or an ethylenically unsaturated group, a linking reaction to the organic polymer component may be run during the elevated temperature compounding step. Other functionalized sol-gel ceramic precursors that can form covalent linkages to the polymer during the elevated temperature compounding step may be alkoxysilanes having an ethylenically unsaturated group, for instance (meth)acryloxyethyltrimethoxysilane, (meth)acryloxypropyltriethoxysilane and 4-trimethoxysilylstyrene. Such functionalized sol-gel ceramic precursor can also be an alkoxysilane having a carbon-linked amino group, for instance 3-aminopropyltriethoxysilane. A SiH functionalized alkoxy silane such as triethoxysilane may be employed to form covalent linkages by hydrosilation.

In other alternatives the functionalized sol-gel ceramic precursor may have hydrolyzable groups other than alkoxide, for instance acyloxide.

In an alternative preparation the functionalized sol-gel ceramic precursor can be an active hydrogen reactive compound, for instance an isocyanate functional alkoxysilane, such as 3-isocyanatopropyltriethoxysilane or 2-isocyanotoethyltriethoxysilane. Epoxy functional ceramic precursors are also suitable, for example glycidoxypropyltrimethoxysilane. Such compounds maybe reacted with polymers that have active hydrogen groups, e.g. hydroxyl, thiol, primary amine, or secondary amine groups, to provide a covalent bond between the polymer and the functionalized alkoxide. The resulting polymer, now functionalized with alkoxysilane or other hydrolyzable silane groups, may then be incorporated into a ceramic network by hydrolysis/condensation of the alkoxysilane groups, suitably together with other sol-gel ceramic precursor compounds such as tetraethoxysilane, tetramethoxysilane, and/or monophenyltriethoxysilane, to produce the organic-inorganic hybrid material from which the inventive particulate materials are prepared. Further examples of preparation of such organic-inorganic hybrids are found in Honma, et al, Solid State Ionics, Vol 118, p 29-36, (1999); Honma, et al, Solid State Ionics, Vol 120, p. 255-264, (1999); Honma, et al, Journal of Membrane Science, Vol 185, p. 83-94, (2001); Huang, Wilkes, Polymer, Vol 30, p 2001-2012, (1989); Young, et al, Polymer, Vol 43, p 6101-6114, (2002); de Zea Bermudez, et al, Chem. Mater., Vol 11, p. 569-580, (1999); Yano, S., et al, Mater Sci Engng, Vol C6, p. 75-90, (1998); and Correia, et al, Solid State Ionics, Vol 156, p. 85-93, (2003).

Alternatively, the organic-inorganic hybrid can be made without covalent bonding therebetween, believed to be through weak hydrogen or Van der Waals bonding, by addition of polymer in an aqueous phase to a sol-gel process, for instance as described in Yano, S., et al, Mater Sci Engng, Vol C6, p. 75-90, (1998).

The polymer incorporated into the organic-inorganic hybrid material may be for instance polyethers such as poly (ethylene oxide), poly(propylene oxide) poly(tetramethyleneoxide), ethylene oxide/propylene oxide copolymers, including block copolymers, and the like; polyesters such as poly(caprylactone); polyamides such as polycaprylactam, block copolymers of polyethers and polyamides, or polyurethanes. In some embodiments the polymer of the organic-inorganic hybrid material is an oligomer or low molecular weight polymer, for instance having a number average molecular weight of about 250 to about 10,000, or about 400 to about 4,000. Suitably the polymer incorporated into the hybrid material will be one that has good compatibility with the thermoplastic polymer with which the hybrid material particles of the invention will be compounded. In some embodiments the polymer is a linear polyether oligomer having terminal amine or hydroxyl groups and that is covalently reacted with ceramic precursor that is functionalized with an organic linking group such as isocyanatopropyltriethoxysilane and then hydrolyzed and condensed with another sol-gel ceramic precursor such as tetraethoxysilane.

The functionalized nanocomposite hybrid can be tailored to include many different types of organic and inorganic species, organic to inorganic ratios as well as specialized physical properties such as electrical conductivity, gas and/or liquid permeability and the like. This can be accomplished by customizing the chemical composition and concentration of the hybrid material precursors.

U.S. Pat. No. 6,825,260 describes a technique for preparing organic-inorganic hybrid materials usable in some embodiments of the present invention.

U.S. patent application Ser. No. 11/094,638, filed Mar. 30, 2005, describes various ways in which sol-gel derived organic-inorganic hybrid materials may be prepared. Such materials may be employed in some embodiments of the invention.

In accordance with the present invention, the condensed hybrid material is a ceramic network that includes polymer interpenetrated therethrough, the polymer optionally also being covalently bound thereto. This hybrid material is dried and granulated into particles of suitable size. Granulating may be by any known process, for instance by grinding, crushing, milling, pounding, or the like. Cryogrinding may be particularly useful for hybrid materials having relatively high organic polymer content, for instance about 25% or more by weight polymer, such as 40-90%.

Suitably the inventive particles are sized to have an average size of less than 10,000 nm, suitably in the range of range of from about 1 to about 1000 nm, for instance from about 3 to about 300 nm or about 10 to about 100 nm. Sieving or other known techniques can be used to classify and fractionate the particles. In addition to sizing the particles to a desirable range, the ratios of components, pH conditions, timing and other techniques of the sol-gel processing may be modified to influence the surface area of the particles obtained.

The particles of the invention may be compounded in compositions with thermoplastic polymers and the compositions processed by standard thermoplastic polymer processing techniques such as extrusion, injection molding, blow molding, roto-molding, stretch-blow molding and the like into formed articles or intermediate products such as tubes or sheets. Intermediate products may be further processed into formed articles. The particles will contribute to the physical properties of the formed articles in accordance with the combined effects of the particle size, the particle surface area, the hybrid material properties and the interaction between the polymer of the hybrid material and the polymer with which it is compounded, as well as the relative ratio of polymer to particle that is employed. The skilled person therefore has the ability to vary properties of such compositions over a very wide range and to more selectively modify physical properties of products formed of the compositions than is presently available from less complex particles such as particles such as fumed or precipitated silicas and the various treated versions thereof currently available commercially.

In addition to thermoplastic polymer compositions, the inventive particles may also be usefully compounded in other types of compositions, such as curable adhesive and/or sealant compositions, paints, coatings and the like.

In some embodiments the polymers for use in compositions with the inventive particles may be one or more of the following: polyester; polyester block copolymers; polycarboxylic acid polymers and copolymers including polyacrylic acids; acetal polymers and copolymers; acrylate and methacrylate polymers and copolymers; cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers; polyamide block copolymers; polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones; polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkylene oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers, ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers of the above.

In some embodiments the inventive particles are compounded with a thermoplastic polyester, for instance poly (ethylene terephthalate), a thermoplastic polyester copolymer for instance Hytrel® or Arnitel® polymers, a thermoplastic polyamide such as nylon 6, nylon 6/6, nylon 9/10, nylon 10, nylon 6/10, nylon 11, or nylon 12, or a polyamide block copolymer such a Pebax® polymer, for instance Pebax® polymers having Shore D durometer grades of about 25 to about 75, or a fluoropolymer.

Without being limited thereto, it is thought that particularly advantageous polymer-polymer interactions will be facilitated when the polymer of the hybrid particle material and the thermoplastic polymer with which the particles are compounded have multiple sites at which interpolymer hydrogen bonding can occur. These interactions can facilitate easier incorporation of the particles into the thermoplastic polymer, better light transparency, toughness and flexibility, thermal formability or the like. Such interactions may occur, for instance, with various combinations of ether, hydroxyl, amide, urethane, urea, and/or carboxyl groups between these polymer moieties. Of course other weak interactions, for instance van der Walls bonding, may also be important to obtaining such benefits from the invention.

Compositions of the invention may be used to form objects of many types. Medical devices of various types are exemplary. Medical devices in which the inventive compositions may be employed include a wide variety of implantable or insertable medical devices, which are implanted or inserted either for procedural uses or as implants. Examples include balloons, catheters (e.g., renal or vascular catheters such as balloon catheters), guide wires, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, tissue bulking devices, sutures, suture anchors, anastomosis clips and rings, tissue staples and ligating clips at surgical sites, cannulae, metal wire ligatures, orthopedic prosthesis, joint prostheses, as well as various other medical devices that are adapted for implantation or insertion into the body. Such medical devices include implantable and insertable medical devices that are used for diagnosis, for systemic treatment, or for the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition. Typical subjects are vertebrate subjects, more typically mammalian subjects and even more typically human subjects.

In some embodiments of the invention, the particles are used in formulations used to produce catheter balloons for dilatation and/or stent delivery to improve the robustness of the balloon during deployment and use.

The invention is illustrated by the following non-limiting example.

EXAMPLE OF FUNCTIONALIZED HYBRID

Materials: Terathane® 650 hydroxyl terminated polytetramethylene ether, number average molecular weight about 650; 3-(triethoxysilyl)propyl isocyanate; hydrochloric acid (HCl) 0.15M, ethanol, tetrahydrofuran (THF), and water.

20.24 g (0.0311 mol) of Terathane® 650 was dissolved in 20 ml anhydrous THF. 13.6331 g (0.0551 mol) of 3-(triethoxysilyl)propyl isocyanate was combined with the Terathane® solution. The mixture was refluxed for 24 hrs. NMR and IR were used to determine that the isocyanate fully reacted. Subsequently 3.1795 g of 0.15M HCL and 20 ml of ethanol were added to the solution. The mixture was stirred for one minute. The mixture was cast into Teflon® beakers and let to air dry. The resultant material had a degradation temperature of about 394° C. as determined by TGA. The DSC results concluded that the material did not melt within a 250° C. sweep. The typical melting point of Terathane 650 is 11-19° C.

When cryo-ground to a suitable particle size as described above, this material may be compounded with a thermoplastic polymer which may then be extruded into components such as catheter tubing or tubing for forming a catheter balloon.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim, regardless of claim sequence, if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A composition comprising
    a) a thermoplastic polymer selected from the group consisting of a polyester block copolymer, a polyamide block copolymer, and mixtures thereof, compounded with
    b) a particulate material comprising separate discrete particles having an average particle size range of about 10,000 nm or less and comprising an organic-inorganic hybrid material comprising a ceramic material network having organic polymer segments distributed throughout the ceramic network.

2. A composition as in claim 1 wherein in said particulate material the ceramic material network comprises an oxide of silicon, iron, vanadium, barium, zirconium, titanium, aluminum, tin, hafnium, rubidium, bismuth, strontium, tantalum, molybdenum, tungsten, rhenium, ruthenium or iridium oxides, or a mixture thereof.

3. A composition as in claim 1 wherein in said particulate material the organic polymer segments are polymer segments having a number average molecular weight of about 250 to about 10,000.

4. A composition as in claim 1 wherein in said particulate material the organic polymer segments are covalently bonded to the ceramic material network.

5. A composition as in claim 1 wherein the average particle size range of said particulate material is from about 1 to about 1000 nm.

6. A composition as in claim 1 wherein in said particulate material the organic-inorganic material is prepared by compounding a sol-gel ceramic precursor with an organic polymer component and subsequently processing the composition in a sol-gel technique to condense the ceramic network.

7. A composition as in claim 6 wherein the polymer component of said particulate material is a organic polymer end-capped with a silyl group having one or more hydrolyzable groups attached to the silicon atom thereof.

8. A composition as in claim 7 wherein the organic polymer component of said particulate material is a polyether polymer.

9. A composition as in claim 7 wherein the organic polymer component of said particulate material is a polyether, polyester, polyamide, block copolymer of polyethers and polyamides, or polyurethane oligomer having a molecular weight of from about 400 to about 4,000, and terminal amine or hydroxyl groups that has been covalently reacted with a ceramic precursor compound that is functionalized with an organic linking group.

10. A thermoformed article prepared from a composition as in claim 1.

11. A medical device having a component formed from a composition as in claim 1.

12. A medical device as in claim 1 wherein the medical device is a balloon, a guide wire, a vena cava filter, a stent, a stent graft, a vascular graft, a cerebral aneurysm filler coil, a myocardial plug, a heart valve, a vascular valve or a tissue engineering scaffold.

* * * * *